(12) United States Patent
Takahashi et al.

(10) Patent No.: US 10,485,410 B2
(45) Date of Patent: Nov. 26, 2019

(54) FLEXIBLE TUBE INSERTION APPARATUS

(71) Applicant: OLYMPUS CORPORATION, Tokyo (JP)

(72) Inventors: Takeshi Takahashi, Hachioji (JP); Yuichi Ikeda, Tama (JP); Shuji Nakamura, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 113 days.

(21) Appl. No.: 15/806,934

(22) Filed: Nov. 8, 2017

(65) Prior Publication Data
US 2018/0064310 A1 Mar. 8, 2018

Related U.S. Application Data

(63) Continuation of application No. PCT/JP2015/063570, filed on May 12, 2015.

(51) Int. Cl.
*A61B 1/00* (2006.01)
*A61B 1/005* (2006.01)

(52) U.S. Cl.
CPC .......... *A61B 1/0052* (2013.01); *A61B 1/0051* (2013.01); *A61B 1/0055* (2013.01);
(Continued)

(58) Field of Classification Search
CPC . A61B 1/0052; A61B 1/0051; A61B 1/00147; A61B 1/00078; A61B 1/0055;
(Continued)

(56) References Cited

U.S. PATENT DOCUMENTS 4,054,128 A * 10/1977 Seufert .............. A61B 1/00082
285/9.1
2014/0230562 A1 8/2014 Yamamoto et al.

FOREIGN PATENT DOCUMENTS

JP S61-037931 A 8/1986
JP H06-181882 A 7/1994
(Continued)

OTHER PUBLICATIONS

Japanese Office Action dated Aug. 21, 2018 in Japanese Patent Application No. 2017-517506.
(Continued)

*Primary Examiner* — Amber R Stiles
(74) *Attorney, Agent, or Firm* — Scully, Scott, Murphy & Presser, P.C.

(57) ABSTRACT

An flexible tube insertion apparatus includes a tubular insertion section including a bending portion and a flexible tube portion, variable stiffness sections to cause a change in a level of a bending stiffness of the flexible tube portion, a variable stiffness control section that controls the change in the bending stiffness by the variable stiffness sections; and a time setting section that sets a time period. The variable stiffness control section causes the bending stiffness of the variable stiffness sections to change in such a manner that the relationship of levels between the bending stiffness of adjacent variable stiffness sections is switched at the set time period when the variable stiffness control section determines that the flexible tube portion is passing through a flexure of the subject.

6 Claims, 11 Drawing Sheets

(52) U.S. Cl.
CPC ........ *A61B 1/00057* (2013.01); *A61B 1/0057* (2013.01); *A61B 1/00078* (2013.01); *A61B 1/00147* (2013.01); *A61B 1/00114* (2013.01)

(58) Field of Classification Search
CPC .............. A61B 1/00057; A61B 1/0057; A61B 1/00114
See application file for complete search history.

(56) References Cited

FOREIGN PATENT DOCUMENTS

| | | | | |
|---|---|---|---|---|
| JP | H06181882 A | * | 7/1994 | ............... A61B 1/00 |
| JP | 2011-245180 A | | 12/2011 | |
| JP | 2013-027466 A | | 2/2013 | |
| JP | 2013-094337 A | | 5/2013 | |
| JP | 2015-016366 A | | 1/2015 | |

OTHER PUBLICATIONS

International Preliminary Report on Patentability together with the Written Opinion from related International Application No. PCT/JP2015/063570 dated Nov. 23, 2017.
International Search Report dated Aug. 11, 2015 issued in PCT/JP2015/063570.

* cited by examiner

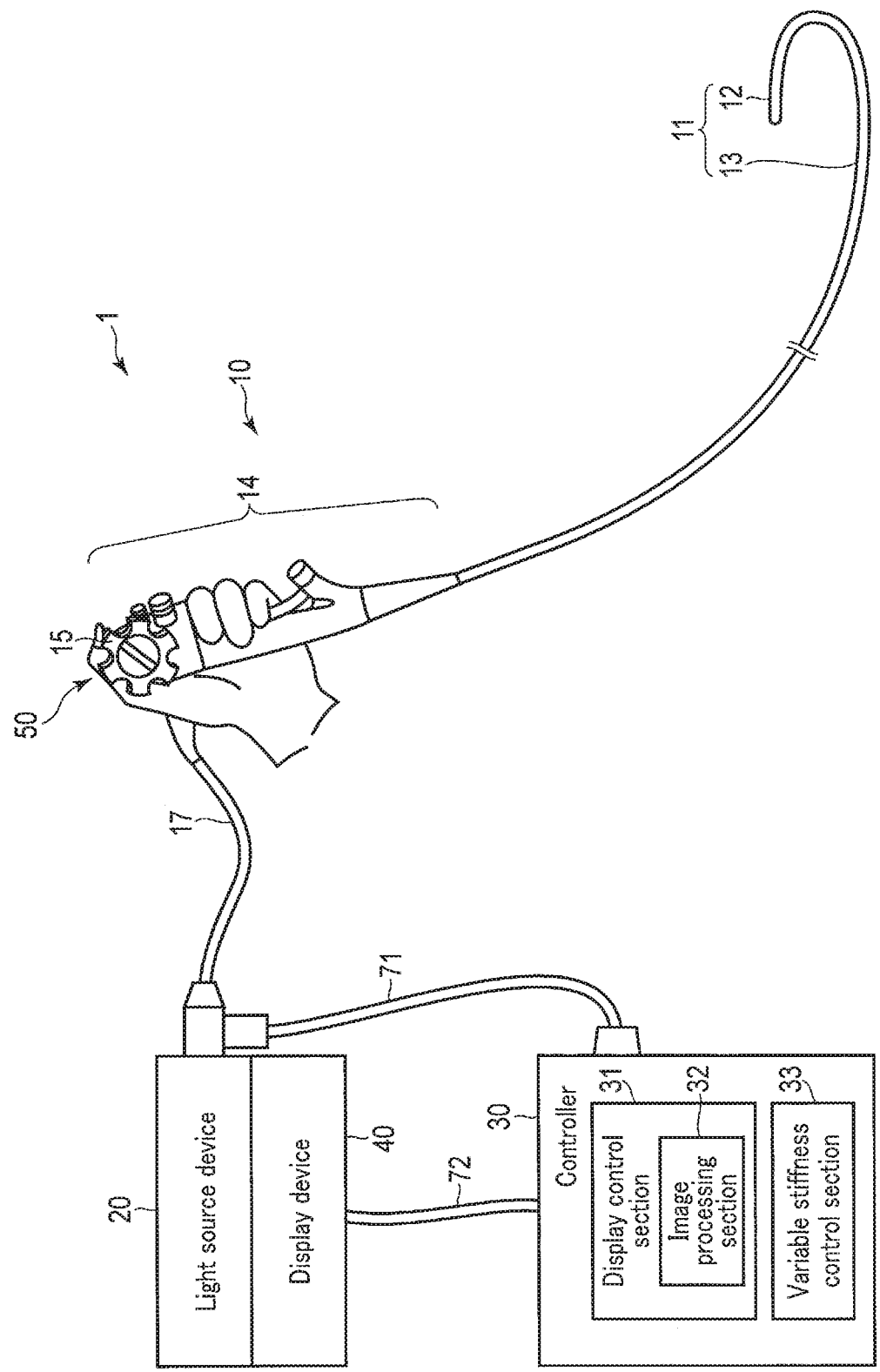
F I G. 1

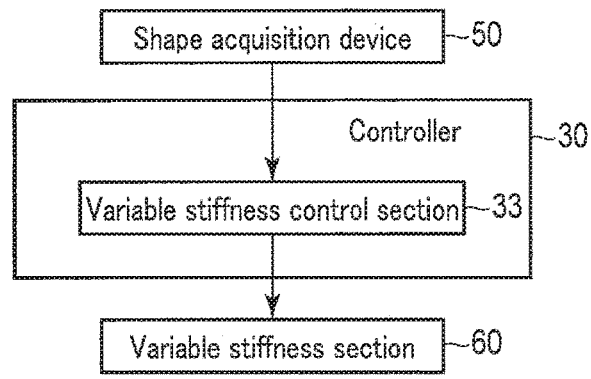
F I G. 7
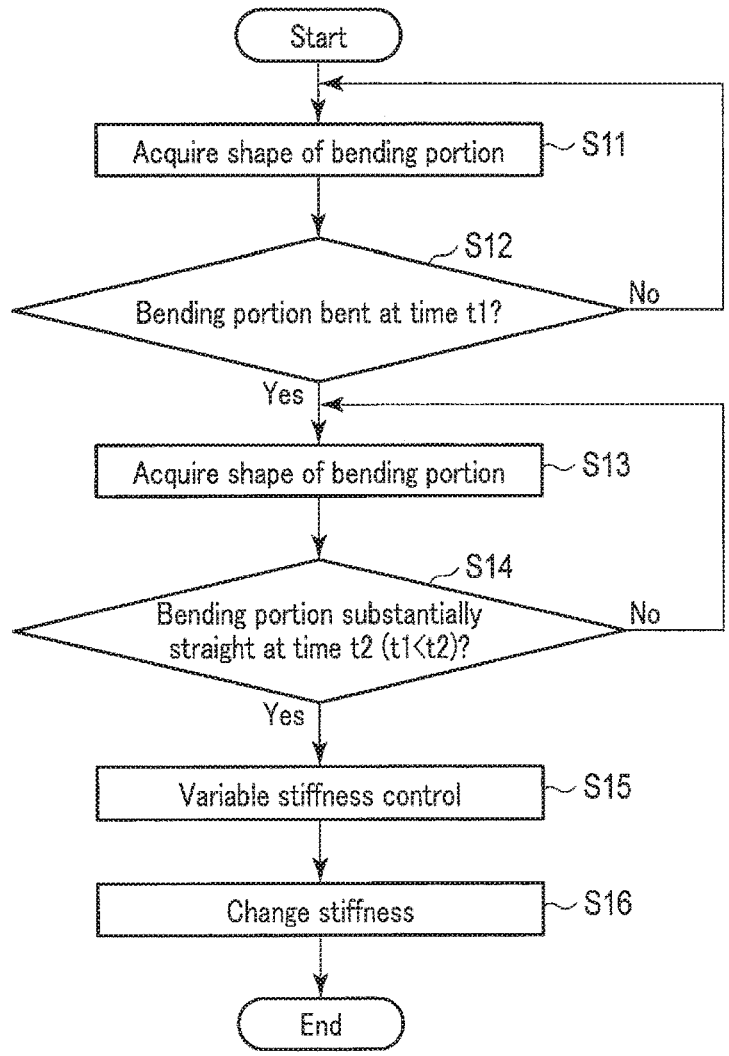
F I G. 8

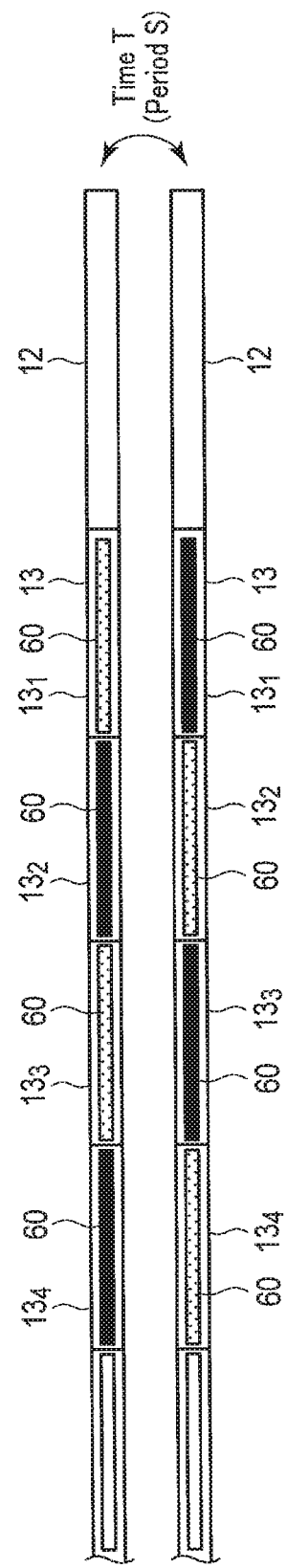
F I G. 11

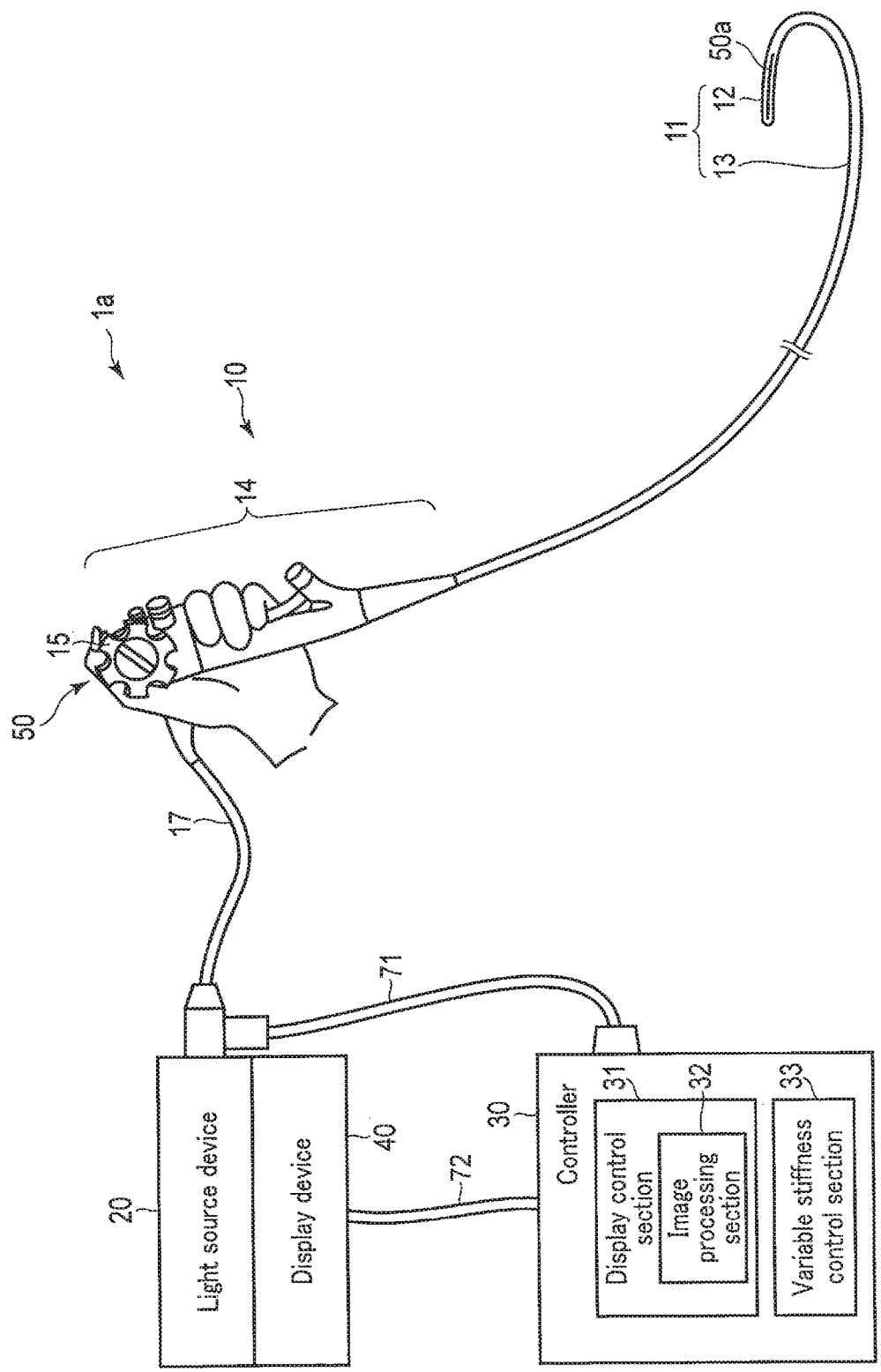
F I G. 12

FLEXIBLE TUBE INSERTION APPARATUS

CROSS-REFERENCE TO RELATED APPLICATIONS

This application is a Continuation Application of PCT Application No. PCT/JP2015/063570, filed May 12, 2015, the entire contents of all of which are incorporated herein by references.

BACKGROUND OF THE INVENTION

1. Field of the Invention

The present invention relates to a flexible tube insertion apparatus comprising an insertion section including a bending portion located distally on the insertion section and a flexible tube portion located proximal to the bending portion.

2. Description of the Related Art

The large intestine roughly consists of the rectum, the colon, and the cecum from the side of the anus. The colon further consists of the sigmoid colon, the descending colon, the transverse colon, and the ascending colon from the rectum side. Normally, the sigmoid colon and the transverse colon are not fixed in the abdomen, and have freedom of movement. When a flexible, elongated insertion section of a flexible tube insertion apparatus (e.g., an endoscope apparatus) is inserted into such an intestinal tract, the insertion section bends along the intestinal wall while passing through the intestinal tract. However, as the insertion section is further advanced from the hand side, the flexible insertion section may be bent in a direction different from the direction in which the force is applied in the intestine, preventing the distal end of the insertion section from passing smoothly. To address such a problem, a technique for facilitating transmission of a force to the direction in which the insertion section should desirably be inserted by increasing the bending stiffness of the insertion section is known. This is implemented either by increasing the bending stiffness of the insertion section itself, or by attaching a member different from the insertion section, such as an overtube (sliding tube), to the insertion section.

However, when the bending stiffness of the entire insertion section is uniformly changed, the stiffness cannot be changed according to the bending state of the insertion section inside the intestinal tract. Accordingly, the insertion section may be stuck in, for example, the sigmoid colon and excessively extend the sigmoid colon, causing distress to the patient. Such an insertion section is inconvenient for insertion into a deep portion.

Jpn. Pat. Appln. KOKOKU Publication No. 61-37931 discloses an endoscope comprising an insertion section including an elongated, flexible tube portion divided into a plurality of areas in the longitudinal direction to cause the areas to have different levels of flexibility. In the endoscope, having different levels of flexibility at the areas of the flexible tube portion allows distress at a patient during insertion to be reduced, thus the ease of insertion is improved.

BRIEF SUMMARY OF THE INVENTION

According to one embodiment of the present invention, an flexible tube insertion apparatus comprises an insertion section to be inserted into a subject and including a bending portion located distally on the insertion section, and a flexible tube portion proximal to the bending portion; a plurality of variable stiffness sections each provided in a corresponding one of a plurality of segments defined in a longitudinal axis direction of the flexible tube portion and configured to cause a change in a level of a bending stiffness of the flexible tube portion on a segment-by-segment basis; a variable stiffness control section that controls the change in the bending stiffness of the flexible tube portion by the variable stiffness sections; and a time setting section that sets a time period at which the bending stiffness is changed by the variable stiffness sections, wherein the variable stiffness control section controls the changes in the bending stiffness of each of the variable stiffness sections in such a manner that the relationship of levels between the bending stiffness of adjacent variable stiffness sections is switched at the time period set by the time setting section when the variable stiffness control section determines that the flexible tube portion is passing through a flexure of the subject based on a bending shape of the bending portion acquired from a shape acquisition section that acquires the bending shape of the bending portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram schematically showing a configuration of an endoscope apparatus according to a first embodiment.

FIG. 7 is a block diagram illustrating variable stiffness control according to the first embodiment.

FIG. 8 is a flowchart illustrating variable stiffness control according to the first embodiment.

FIG. 11 is a diagram illustrating periodic switching of a bending stiffness of variable stiffness sections according to the third embodiment.

FIG. 12 is a diagram schematically showing a configuration of an endoscope apparatus according to a fourth embodiment.

DETAILED DESCRIPTION OF THE INVENTION

First Embodiment

Figure 2:
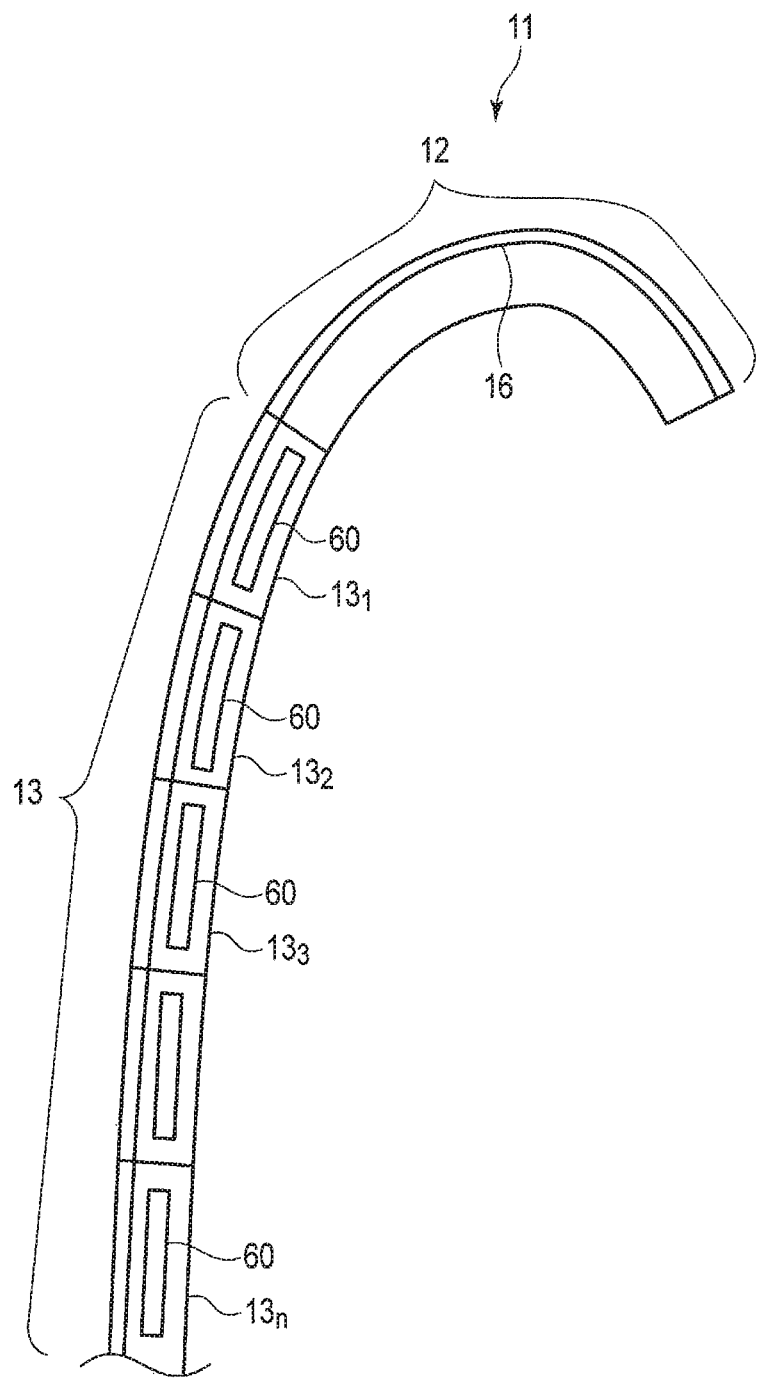
FIG. 2 is an enlarged view schematically showing a bending portion and a flexible tube portion.

The first embodiment of the present invention will be described with reference to FIGS. 1 to 8.

FIG. 1 is a diagram schematically showing a configuration of an endoscope apparatus 1, which is a flexible tube insertion apparatus. The endoscope apparatus 1 comprises an endoscope 10, a light source device 20, a controller 30, and a display device 40.

The endoscope 10 includes a tubular insertion section 11 to be inserted into a subject, and an operation section 14 located proximal to the insertion section 11. The endoscope 10 is, for example, a colonoscope. That is, the subject is the large intestine (intestinal tract).

The insertion section 11 includes a bending portion 12 located distally on the insertion section 11 and a flexible tube portion 13 located proximal to the bending portion 12. The bending portion 12 incorporates, for example, an illumination optical system (illumination window), an observation optical system (observation window), and an image sensor, which are not shown in the drawings. The flexible tube portion 13 is an elongated tube that is bendable and flexible.

The operation section 14 is the portion of the endoscope 10 that is gripped by the user, as shown in FIG. 1. The operation section 14 includes an angle knob 15, which is a bending operation section. The angle knob 15 is coupled to the bending portion 12 via an angle wire 16 (not shown in FIG. 1), which has at least one pulling member inserted through the insertion section 11 in its longitudinal direction (axial direction). FIG. 2 shows the angle wire 16 extending from the bending portion 12 to the flexible tube portion 13 inside the insertion section 11 along its inner surface. A distal end of the angle wire 16 is fixed to the bending portion 12. When the user rotates the angle knob 15, the angle wire 16 coupled thereto is moved, causing the bending portion 12 to be bent in a desired direction. Let us assume, for example, that two angle wires are vertically arranged relative to the central axis of the insertion section 11 to maintain a 180-degree positional relationship. In this case, when one of the angle wires is pulled in by the user's rotation of the angle knob 15, the bending portion 12 is bent in an upward direction, and when the other angle wire is pulled in, the bending portion 12 is bent in a downward direction.

A shape acquisition section 50, which acquires the bending shape (the bend angle, etc.) of the bending portion 12, is provided at the operation section 14. The shape acquisition section 50 includes, for example, a rotary encoder whose axis of rotation is attached to the axis of rotation of the angle knob 15. The rotary encoder is a rotation angle sensor that converts a displacement in rotation angle into an electric signal and outputs the electric signal. By thus detecting the rotation angle, the rotation amount, or the rotation position of the angle knob 15, the shape acquisition section 50 acquires the bending shape of the bending portion 12. The shape acquisition section 50 is not limited to a rotary encoder. The shape acquisition section 50 may be configured to acquire the bending shape of the bending portion 12 by a detection method of detecting an amount of movement of the angle wire 16 that pulls the bending portion 12 and calculating the bending state of the bending portion 12.

FIG. 2 is an enlarged view schematically showing the bending portion 12 and the flexible tube portion 13. For convenience, let us assume that the flexible tube portion 13 comprises a plurality of continuous segments (virtual units into which the flexible tube portion 13 is evenly divided as viewed in the longitudinal direction) defined in the longitudinal axis direction thereof. In FIG. 2, segments $13_1$, $13_2$, $13_3$, ..., and $13_n$ of the flexible tube portion 13 are shown. A variable stiffness section 60 is provided in each of the segments. The variable stiffness section 60 is a variable stiffness actuator that allows to change the bending stiffness of the flexible tube portion 13 on a segment-by-segment basis.

Referring back to FIG. 1, the endoscope 10 is connected to the light source device 20 via a universal cord 17 extending proximally from the operation section 14. The universal cord 17 includes a light guide (optical fiber) connected to the illumination optical system, an electric cable connected to the image sensor, a variable stiffness section control signal cable, a shape acquisition section signal cable, etc. The light source device 20 supplies light to be emitted from the illumination window in the distal end surface of the bending portion 12 via the light guide.

The controller 30 is formed of a device including a CPU and the like. The controller 30 includes a display control section 31 including an image processing section 32, and a variable stiffness control section 33. The display control section 31 is connected to the electric cable in the universal cord 17 via a cable 71, and thus connected to the endoscope 10 (the image sensor in the bending portion 12). The display control section 31 is also connected to the display device 40 via a cable 72. The variable stiffness control section 33 is connected to the variable stiffness section 60 via the cable 71 and the variable stiffness section control signal cable included in the universal cord 17. The variable stiffness control section 33 is connected to the shape acquisition section 50 via the cable 71 and the shape acquisition section signal cable included in the universal cord 17.

Figure 3:
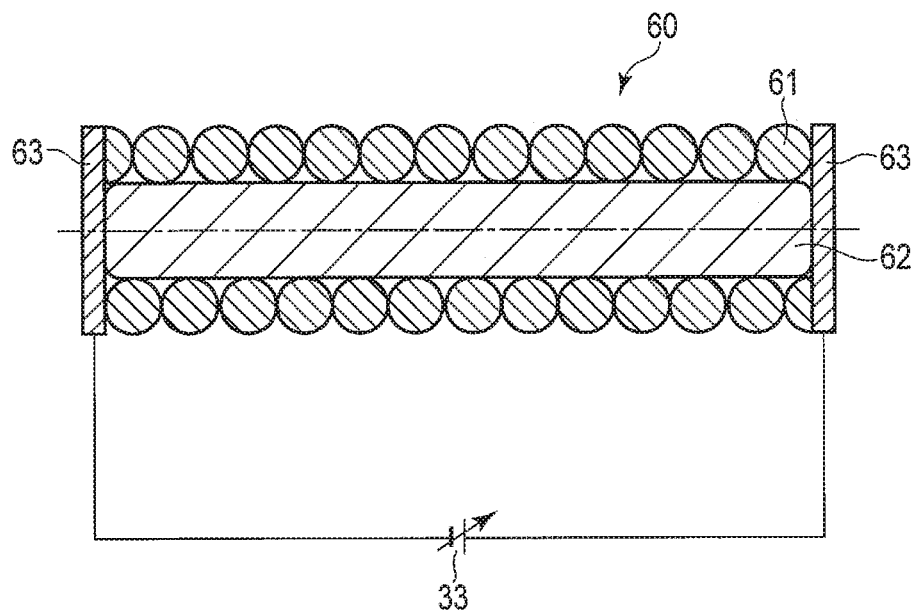
FIG. 3 is a diagram schematically showing an example of a configuration of a variable stiffness section.

FIG. 3 is a diagram schematically showing an example of a configuration of the variable stiffness section 60. The variable stiffness section 60 includes a coil pipe 61 formed of a metal wire, an electroactive polymer artificial muscle (EPAM) 62 encapsulated in the coil pipe 61, and electrodes 63 provided on both ends of the coil pipe 61. The variable stiffness section 60 is connected to the variable stiffness control section 33, and thus a voltage may be applied from the variable stiffness control section 33 to the EPAM 62 in the coil pipe 61 via the electrodes 63. The EPAM 62 is an actuator that extends and contracts when a voltage is applied and changes its stiffness. The variable stiffness section 60 is incorporated into the flexible tube portion 13 in such a manner that the central axis of the coil pipe 61 coincides with or is parallel to the central axis of the flexible tube portion 13.

Figure 4:
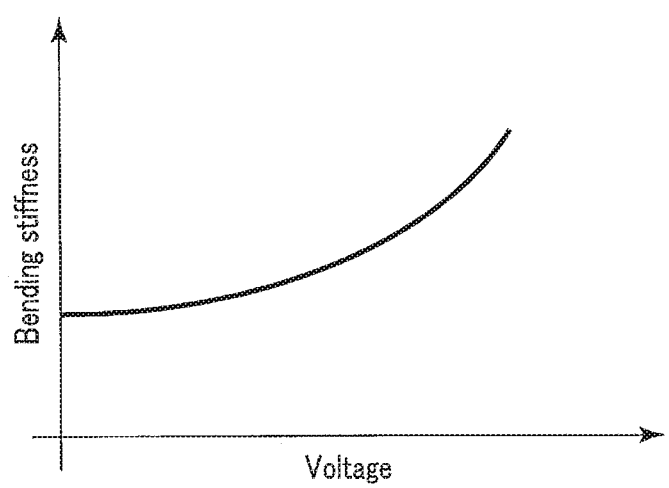
FIG. 4 is a diagram showing a voltage-bending stiffness characteristic of the variable stiffness section.

The electrodes 63 (the EPAM 62) of the variable stiffness section 60 are applied with a voltage from the variable stiffness control section 33 via the cable 71 and the electric cable in the universal cord 17. When such a voltage is applied, the EPAM 62 tends to extend its diameter with the central axis of the coil pipe 61 at its center. However, the EPAM 62 is surrounded by the coil pipe 61, and is restrained from extending its diameter. Accordingly, the bending stiffness of the variable stiffness section 60 increases as the value of the applied voltage increases, as shown in FIG. 4. That is, when the variable stiffness control section 33 changes the voltage applied to the variable stiffness section 60, the stiffness of the variable stiffness section 60 changes, and the bending stiffness of the flexible tube portion 13 incorporating the variable stiffness section 60 also changes.

The above-described configuration of the variable stiffness section 60 is merely an example. The variable stiffness section 60 is not limited to the one using the EPAM 62, and may have any configuration that allows the bending stiffness to be changed in response to a control signal from the variable stiffness control section 33.

Next, the operation of the endoscope apparatus 1, which is colonoscopy in this case, will be described.

Let us assume that, at the start of insertion, the flexible tube portion 13 has a predetermined bending stiffness value that is neither the minimum bending stiffness value nor the maximum bending stiffness value of the variable stiffness section 60. That is, each segment of the flexible tube portion 13 may be stiffened or softened, compared to the state at the start of insertion, by causing the bending stiffness of the variable stiffness section 60 to change in response to the control signal from the variable stiffness control section 33.

The insertion section 11 of the endoscope 10 is inserted by the user into an intestinal tract, which is a subject to be examined (from the anus through the rectum into the colon). The insertion section 11 passes through the intestinal tract while bending to follow the shape inside of the intestinal tract. An optical image of the observation target acquired by the observation optical system on the distal end surface of the bending portion 12 is converted into an electric signal by the image sensor. The electric signal is output to the display control section 31 of the controller 30. The display control section 31 causes the image processing section 32 to generate an image signal of the observation target on the basis of the output electric signal. The display control section 31 then causes the display device 40 to display an image of the observation target on the basis of the generated image signal.

Figure 5:
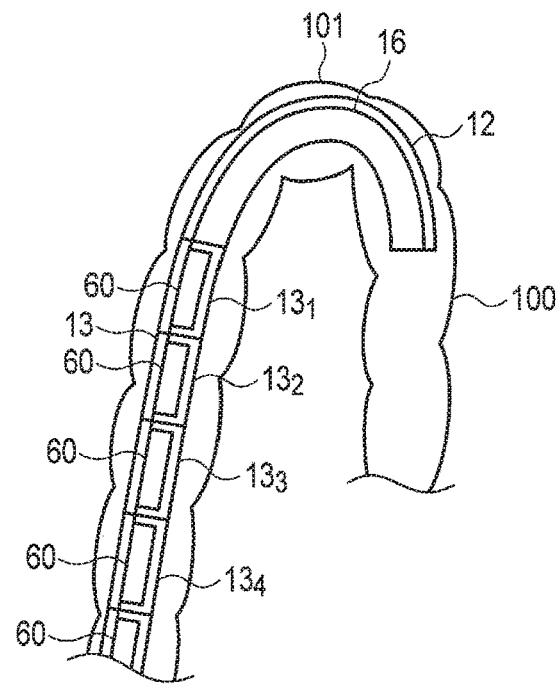
FIG. 5 is a diagram schematically showing an example of a state in which an insertion section is inserted into the large intestine (the bending portion is bent along an intestinal tract) according to the first embodiment.
Figure 6:
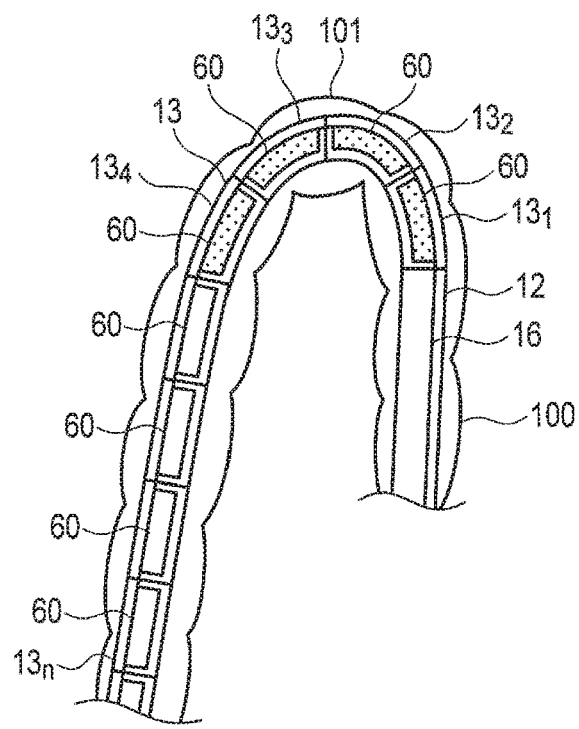
FIG. 6 is a diagram schematically showing an example of a state in which the insertion section is inserted into the large intestine (the bending portion is substantially straight along the intestinal tract and the flexible tube portion is bent along the intestinal tract) according to the first embodiment.

FIGS. 5 and 6 schematically show an example of the insertion section 11 inserted into the large intestine. At first, the bending portion 12 located distally on insertion section 11 is in a substantially straight state and passes through a substantially straight area in an intestinal tract 100. When the bending portion 12 reaches a flexure 101 (e.g., the sigmoid colon) in the intestinal tract 100, the bending portion 12 passes while bending to follow the shape of the curvature of the flexure 101, as shown in FIG. 5. When the bending portion 12 passes through the flexure 101, the bending portion 12 is bent along the shape of the flexure 101 either by causing the angle knob 15 of the operation section 14 to rotate by user, or by applying an external force. Accordingly, the bending portion 12 is necessarily bent when the bending portion 12 passes through the flexure 101.

When the bending portion 12 further advances and has passed through the flexure 101, the flexible tube portion 13 reaches the flexure 101, as shown in FIG. 6. At this time, the bending portion 12, which has already passed through the flexure 101, has substantially straight to follow the substantially straight shape of the intestinal tract 100 in the forward direction of passage relative to the flexure 101. Thus, when the bending portion 12 is bent and then has substantially straight, it means that the flexible tube portion 13 continuous with the bending portion 12 and located proximal to the bending portion 12 is just passing through the flexure 101 (located near the flexure 101), namely, that the bending stiffness of the flexible tube portion 13 should be changed.

Therefore, according to the present embodiment, the shape acquisition section 50 acquires the bending shape of the bending portion 12 during insertion, and the variable stiffness control section 33 determines whether or not the bending stiffness of the flexible tube portion 13 should be changed based thereon. Hereinafter, variable stiffness control of the flexible tube portion 13 according to the present embodiment will be described.

FIG. 7 is a block diagram illustrating variable stiffness control according to the first embodiment. FIG. 8 is a flowchart illustrating variable stiffness control according to the first embodiment. step S11, the shape acquisition section 50 acquires the rotation angle of the angle knob 15 of the operation section 14 at a certain time t1, namely, information about the bending shape (the state of bending) of the bending portion 12. The information acquired at the shape acquisition section 50 is output to the variable stiffness control section 33 of the controller 30, as shown in FIG. 7. The acquired information may be displayed on the display device 40 via the display control section 31.

The variable stiffness control section 33 determines the bending state of the bending portion 12 on the basis of the output information. Specifically, the variable stiffness control section 33 determines, at step S12, whether or not the bending portion 12 is bent to a predetermined degree or higher at the time t1. Hereinafter, the determination in step S12 will be referred as a first bending state determination. At this step S12, it is determined whether or not the bending portion 12, which passes through the intestinal tract 100, is just passing through the flexure 101 or located at the flexure 101, as shown in FIG. 5. The predetermined degree of bending for the first bending state determination may be conveniently set by the user, or a preset value according to the subject may be used for the first bending state determination.

At step S12, when it is determined that the bending portion 12 is bent to a predetermined degree or higher at the time t1 (Yes), the processing proceeds to step S13, and the variable stiffness control section 33 acquires information about the bending shape of the bending portion 12 at a time t2 later than the time t1 (t1<t2) from the shape acquisition section 50. When it is determined that the bending portion 12 is not bent (No), the processing returns to step S11, and the variable stiffness control section 33 acquires information about the bending shape of the bending portion 12 again at a new time t1 from the shape acquisition section 50.

After the variable stiffness control section 33 has acquired information about the bending shape of the bending portion 12 at step S13, the variable stiffness control section 33 determines, at step S14, whether or not the bending portion 12 is substantially straight at the time t2. Hereinafter, the determination in the step S14 will be referred as a second bending state determination. At this step S14, it is determined whether the bending portion 12 has already passed through the flexure 101, as shown in FIG. 6, and has substantially straight to follow the shape of the intestinal tract 100 in the forward direction of passage relative to the flexure 101.

If it is determined, at step S14, that the bending portion 12 is substantially straight at the time t2 (Yes), the processing proceeds to step S15. If it is determined that the bending portion 12 is not substantially straight (No), the processing returns to step S13, and the variable stiffness control section 33 acquires information about the bending shape of the bending portion 12 again at a new time t2 from the shape acquisition section 50.

At step S15, the variable stiffness control section 33 transmits a control signal to the variable stiffness sections 60 to change the bending stiffness of the variable stiffness section 60 arranged in each of the segments of the flexible tube portion 13. Preferably, the segment including the variable stiffness section 60 whose bending stiffness is to be changed should be at least one segment including the segment next to the bending portion 12 among the flexible tube portion 13.

The variable stiffness control section 33 transmits, for example, a control signal to the variable stiffness sections 60 to control the bending stiffness of each variable stiffness section 60, in such a manner that at least one variable stiffness section 60 in the vicinity of the bending portion 12 or next to the bending portion 12 among the flexible tube portion 13 has a low bending stiffness value, that is, at least one segment corresponding to the at least one variable stiffness section 60 allows to be softened. In the example shown in FIG. 6, the variable stiffness control section 33 causes the variable stiffness sections 60 provided in the respective four segments in the flexible tube portion 13, namely, segment $13_1$ closest to the bending portion 12 to segment $13_4$, to have a low bending stiffness value. In FIG. 6, the variable stiffness sections 60 to be caused to be a low bending stiffness value are dotted. The number of segments whose bending stiffness is to be changed is not limited to the above-described number, and may be conveniently set depending on the axial lengths of the segments and the variable stiffness sections 60, the general length of the flexure 101, and the like.

For example, when the bending stiffness of the entire flexible tube portion 13 is wholly high, the flexible tube portion 13 may not be properly bent in the flexure 101, causing extension of the intestinal wall at the flexure 101. This causes distress to the patient. Various approaches show that the force that bends the flexible tube portion 13 during insertion is reduced when the hand side (proximal side) of the flexible tube portion 13 is soft, and that the force is transmitted to the distal side more easily when the distal side has a bending stiffness higher than that of the proximal side. Accordingly, the variable stiffness control section 33 transmits, for example, a control signal for reducing the bending stiffness value of the flexible tube portion 13 in the vicinity of the flexure 101 (e.g., segments $13_1$ to $13_4$) to the corresponding variable stiffness section 60. This allows the segment of the flexible tube portion 13 in the vicinity of the flexure 101 to be soft and easily bent along the shape of the flexure 101. Since the segment located proximally on the flexible tube portion 13 is stiffer than the segment located distally on the flexible tube portion 13, the force pressing the insertion section 11 toward the direction of passage is easily transmitted.

Alternatively, the variable stiffness control section 33 may transmit a control signal to the variable stiffness sections 60 to control the bending stiffness of each variable stiffness section 60, in such a manner that at least one variable stiffness section 60 in the vicinity of the bending portion 12 or next to the bending portion 12 has a high bending stiffness, that is, at least one segment corresponding to the at least one variable stiffness section 60 allows to be stiffened.

At step S16, the bending stiffness of each of the variable stiffness sections 60 is changed, and thereby the variable stiffness control ends up.

In the description given above, the variable stiffness control section 33 acquires information about the bending shape of the bending portion 12 from the shape acquisition section 50 at steps S11 and S13. However, the shape acquisition section 50 may constantly acquire information about the bending shape of the bending portion 12 during insertion, and the variable stiffness control section 33 may also be configured to constantly acquire information about the bending shape of the bending portion 12 from the shape acquisition section 50. Accordingly, the variable stiffness control section 33 may perform the first bending state determination and the second bending state determination while immediately acquiring information about the bending shape of the bending portion 12 during insertion.

In the present embodiment, since a sensor that detects the bending shape of the flexible tube portion 13 is not arranged in the flexible tube portion 13, the bending shape itself of the flexible tube portion 13 during insertion cannot be determined. In the present embodiment, however, a shape acquisition section 50 is provided in the operation section 14 to acquire the bending shape of the bending portion 12. Thus, the bending state of the bending portion 12 located distally on the insertion section 11, which is bent by a rotation operation of the angle knob 15 of the operation section 14 is determined.

On the basis of the bending state of the bending portion 12 acquired by the shape acquisition section 50, the variable stiffness control section 33 determines whether or not the bending portion 12 has passed through the flexure 101 in the intestinal tract 100, and whether or not the bending portion 12 has become substantially straight after the passage. When it is determined that the bending portion 12 has become substantially straight after passing through the flexure 101, the flexible tube portion 13 continuous with the bending portion 12 and located proximal to the bending portion 12 is passing just through the flexure 101, that is, located in the vicinity of the flexure 101. In the present embodiment, although the bending shape of the flexible tube portion 13 cannot be directly acquired, the bending state of the bending portion 12 next to the flexible tube portion 13 is acquired. Using the acquired bending state as a trigger, the variable stiffness control section 33 determines that the flexible tube portion 13 is passing through the flexure 101, namely, that the bending stiffness of the flexible tube portion 13 should be changed.

The variable stiffness control section 33 controls the bending stiffness of each of the variable stiffness sections 60 in such a manner that the bending stiffness of the variable stiffness section 60 provided in at least one segment of the flexible tube portion 13 passing through the flexure 101 is changed. This allows, for example, the segment of the flexible tube portion 13 located in the vicinity of the flexure 101 to be easily bent along the shape of the flexure 101, thereby improving the ease of insertion.

In the present embodiment, since no sensor is provided in the flexible tube portion 13 to acquire its bending shape, the flexible tube portion 13 does not need to be increased in diameter. It is thus possible to provide a flexible tube insertion apparatus including the flexible tube portion 13 that has a small diameter and achieves an improved ease of insertion.

According to the present embodiment, it is possible to provide a flexible tube insertion apparatus that changes the bending stiffness of the flexible tube portion 13 to follow the shape of curvature in the subject and thereby achieves an improved ease of insertion, by acquiring the bending shape of the bending portion 12 using the shape acquisition section 50 provided in the operation section 14, thus determining the bending state of the flexible tube portion 13 on the basis of the acquired bending shape, without providing a sensor in the flexible tube portion 13. It is also possible to provide a flexible tube insertion apparatus that reduces distress to the patient.

Hereinafter, the second to fifth embodiments of the present invention will be described. In the following, detailed explanations of the structures and operations similar to those in the first embodiment will be omitted, and only matters different from those of the first embodiment will be described.

Second Embodiment

The second embodiment of the present invention will be described with reference to FIG. 9.

Figure 9:
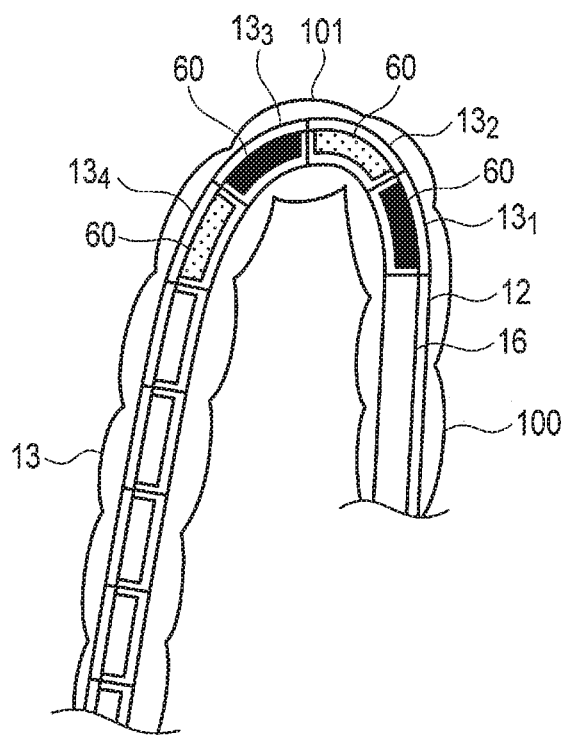
FIG. 9 is a diagram schematically showing an example of a state in which an insertion section is inserted into the large intestine (a bending portion is substantially straight along an intestinal tract and a flexible tube portion is bent along the intestinal tract) according to a second embodiment.

FIG. 9 is a diagram schematically showing an example of a state in which the insertion section 11 is inserted into the large intestine according to the second embodiment. FIG. 9 is a view substituting for FIG. 6 of the first embodiment.

Of the steps of the variable stiffness control flow shown in FIG. 8, only the specific control of the variable stiffness control at step S15 is different in the second embodiment from that of the first embodiment. In the second embodiment, at step S15, the variable stiffness control section 33 transmits a control signal for controlling the bending stiffness of each variable stiffness section 60 to the variable stiffness sections 60 in such a manner that a variable stiffness section 60 with a low bending stiffness value and a variable stiffness section 60 with a high bending stiffness value are alternately arranged proximal to flexible tube portion 13 along the axial direction of the insertion section 11 in the part of the flexible tube portion 13 in the vicinity of the bending portion 12 or next to the bending portion 12.

In the example shown in FIG. 9, the bending stiffness of the variable stiffness section 60 provided in each of four segments 13$_1$ to 13$_4$ is changed, in such a manner that the segment 13$_1$ closest to the bending portion 12 in the flexible tube portion 13 allows to be stiffened (the corresponding variable stiffness section 60 has a high bending stiffness value), the segment 13$_2$ adjacent thereto allows to be softened (the corresponding variable stiffness section 60 has a low bending stiffness value), the segment 13$_3$ adjacent thereto allows to be stiffened, and the segment 13$_4$ adjacent thereto allows to be softened. In FIG. 9, the variable stiffness sections 60 to be caused to be a high bending stiffness value are solidly shaded, and the variable stiffness sections 60 to be caused to be a low bending stiffness value are dotted. Thus, stiff segments and soft segments are alternately set in the flexible tube portion 13 located in the vicinity of the flexure 101. In the present embodiment, the number of segments whose bending stiffness is to be changed is not limited to the above-described number, and may be conveniently set.

In the example shown in FIG. 9, the bending stiffness value of the variable stiffness section 60 provided in the segment 13$_1$ of the flexible tube portion 13 is set to be high, and the variable stiffness control section 33 controls the bending stiffness in such a manner that a stiff segment and a soft segment are alternately arranged. However, the control may be performed in such a manner that a flexible segment and a stiff segment are alternately arranged by setting the bending stiffness value of the variable stiffness section 60 provided in the segment 13$_1$ to be low.

According to the present embodiment, the variable stiffness control section 33 transmits a control signal for controlling the bending stiffness of each variable stiffness section 60 to the variable stiffness sections 60 in such a manner that a plurality of segments of the flexible tube portion 13 are alternately set to soft and stiff states along the axial direction of the insertion section 11. By such variable stiffness control, it is possible to obtain a flexible tube insertion apparatus that ensures the ease of insertion appropriate for the bending state of the flexible tube portion 13 during insertion.

Third Embodiment

The third embodiment of the present invention will be described with reference to FIGS. 10 and 11.

Figure 10:
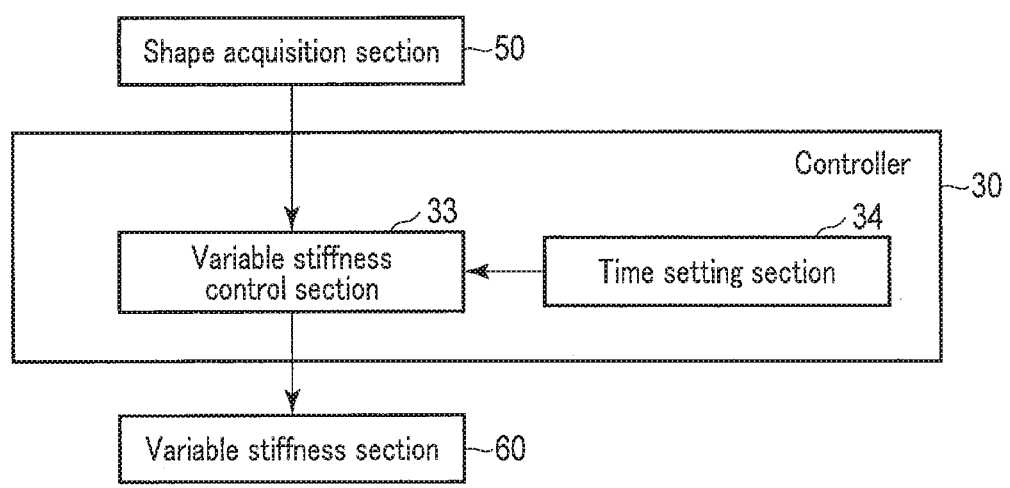
FIG. 10 is a block diagram illustrating variable stiffness control according to a third embodiment.

FIG. 10 is a block diagram illustrating variable stiffness control according to the third embodiment. In the third embodiment, the controller 30 includes a time setting section 34, in addition to the display control section 31, the image processing section 32, and the variable stiffness control section 33. A time T at which the bending stiffness value of each of the variable stiffness sections 60 is changed, that is, period S at which switching is made between a stiff state and a soft state is input to the time setting section 34 from, for example, an input section not shown in the drawings. The time T may be conveniently set by the user, or may be set in advance in compliance with the endoscope 10 to be used.

Of the steps of the variable stiffness control flow shown in FIG. 8, only the specific control of the variable stiffness control at step S15 is different in the third embodiment from that of the first embodiment. In the third embodiment, the variable stiffness control section 33 reads out a time T or period S set by the time setting section 34 at step S15. As in the second embodiment, the variable stiffness control section 33 then transmits a control signal for changing the bending stiffness of each variable stiffness section 60 to the variable stiffness sections 60 in such a manner that a variable stiffness section 60 with a low bending stiffness value and a variable stiffness section 60 with a high bending stiffness value are alternately arranged proximal to the flexible tube portion 13. Thereby, a soft segment 13$_1$ and 13$_3$ including a variable stiffness section 60 with a low bending stiffness value and a stiff segment 13$_2$ and 13$_4$ including a variable stiffness section 60 with a high bending stiffness value are alternately set in the flexible tube portion 13, as shown, for example, by the upper part in FIG. 11. In FIG. 11, the variable stiffness sections 60 to be caused to be a low bending stiffness value are dotted, and the variable stiffness sections 60 to be caused to be a high bending stiffness value are solidly shaded.

The variable stiffness control section 33 further transmits a control signal for changing the bending stiffness of each variable stiffness section 60 to the variable stiffness sections 60 to periodically switch the relationship of levels between the bending stiffness values of adjacent variable stiffness sections 60 at a time T or period S. Thereby, a soft segment $13_1$ and $13_3$ including a variable stiffness section 60 with a high bending stiffness value, and a stiff segment $13_2$ and $13_4$ including a variable stiffness section 60 with a low bending stiffness value, are alternately set in the flexible tube portion 13 after the time T, as shown, for example, by the lower part in FIG. 11. Thus, the variable stiffness control section 33 automatically switches the relationship of levels between the bending stiffness of adjacent variable stiffness sections 60 each time T set by the time setting section 34.

As a matter of course, the original relationship between the bending stiffness values of the segments $13_1$ and $13_3$ and the bending stiffness value of the segments $13_2$ and $13_4$ of the flexible tube portion 13 may be opposite to the above-described relationship, and the number of segments whose bending stiffness is to be changed is not limited to the above-described number.

According to the present embodiment, a plurality of segments of the flexible tube portion 13 are alternately set to a stiff state and a soft state along the axial direction of the insertion section 11, and are automatically and periodically switched between the stiff and soft states at a preset time period. By performing such variable stiffness control, even if one of the segments of the flexible tube portion 13 has a bending stiffness that is not appropriate for passage through the flexure 101 at a certain timing, that segment will have a bending stiffness appropriate for passage through the flexure 101 at a timing when the bending stiffness is switched next. Such switching allows the user to advance the flexible tube portion 13, thus improving the ease of insertion.

Moreover, such periodic switching allows the force at the hand side to be easily transmitted to the distal end when the insertion section 11 is advanced. Furthermore, the distress on the large intestine is reduced, and the time required for insertion is reduced. Thus, according to the present embodiment, it is possible to provide a flexible tube insertion apparatus that conforms to complicated shapes of curvature inside of the intestinal tract and ensures the ease of insertion.

Fourth Embodiment

The fourth embodiment of the present invention will be described with reference to FIGS. 12 to 14.

FIG. 12 is a diagram schematically showing a configuration of an endoscope apparatus 1a according to the fourth embodiment. In the endoscope apparatus 1a, a shape acquisition section 50a for acquiring the bending shape of the bending portion 12, in place of the shape acquisition section 50 of the first embodiment, is provided in the bending portion 12 at the distal end of the insertion section 11. The shape acquisition section 50a comprises a known sensor configured of one of a sensor using magnetism (a magnetic sensor), a sensor using ultrasound waves (an ultrasonic sensor), a sensor using loss of light (an optical fiber sensor), a sensor using distortion (a distortion sensor), and a sensor using an X-ray absorbent material, or a combination thereof.

The shape acquisition section 50a is arranged at least a part of the bending portion 12. That is, the shape acquisition section 50a may be arranged across the entire length of the bending portion 12 or only in a part thereof. The shape acquisition section 50a is connected to the variable stiffness control section 33 of the controller 30 via the cable 71 and the shape acquisition section signal cable included in the universal cord 17.

Figure 13:
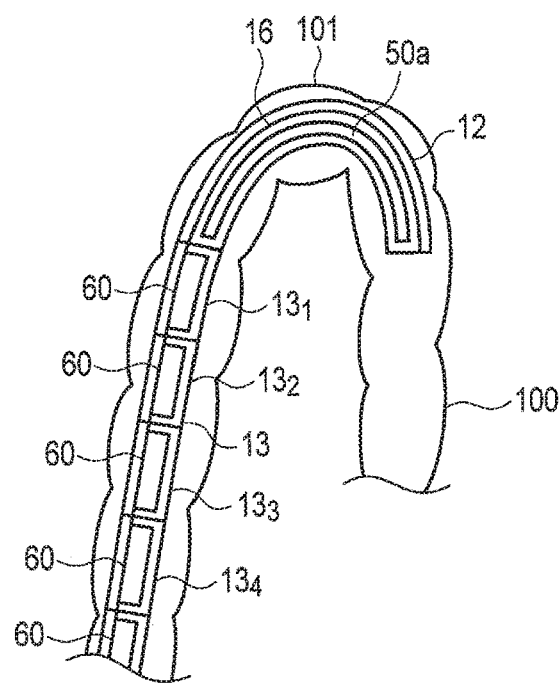
FIG. 13 is a diagram schematically showing an example of a state in which an insertion section is inserted into the large intestine (a bending portion is bent along an intestinal tract) according to the fourth embodiment.
Figure 14:
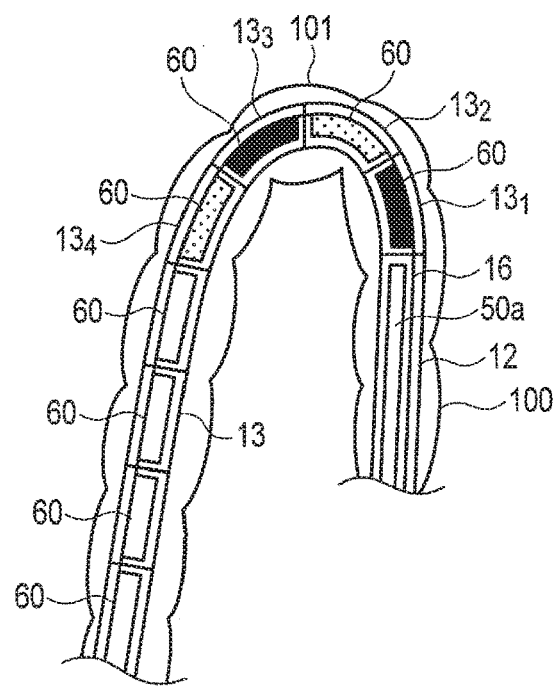
FIG. 14 is a diagram schematically showing an example of a state in which the insertion section is inserted into the large intestine (the bending portion is substantially straight along the intestinal tract and a flexible tube portion is bent along the intestinal tract) according to the fourth embodiment.

FIGS. 13 and 14 are diagrams schematically showing an example of the state in which the insertion section 11 is inserted into the large intestine according to the fourth embodiment. FIG. 13 corresponds to FIG. 5 in the first embodiment, and FIG. 14 corresponds to FIG. 9 in the second embodiment.

The flow of the variable stiffness control according to the fourth embodiment is similar to the flow shown in FIG. 8, and the specific control of the variable stiffness control at step S15 is similar to that of the second embodiment. According to the present embodiment, the variable stiffness control section 33 performs the first bending state determination and the second bending state determination on the basis of the bending shape of the bending portion 12 acquired by the shape acquisition section 50a provided in the bending portion 12. The variable stiffness control section 33 transmits a control signal for controlling the bending stiffness of each variable stiffness section 60 to the variable stiffness sections 60, in such a manner that a variable stiffness section 60 with a low bending stiffness value and a variable stiffness section 60 with a high bending stiffness value are alternately arranged proximal to the flexible tube portion 13 in the part of the flexible tube portion 13 in the vicinity of the bending portion 12 or next to the bending portion 12.

In the present embodiment, the actual bending shape of the bending portion 12 is detected by the shape acquisition section 50a provided in the bending portion 12, instead of detecting the bending shape of the bending portion 12 on the basis of the amount of rotation operation of the angle knob 15 of the operation section 14. Thereby, the bending shape of the bending portion 12 is more reliably detected, allowing the variable stiffness control section 33 to perform the first bending state determination and the second bending state determination based thereon. It is thus possible to provide a flexible tube insertion apparatus capable of changing the bending stiffness of the flexible tube portion 13 on the basis of the more reliable detection of the bending shape.

Furthermore, according to the present embodiment, the shape acquisition section 50a is arranged only in the bending portion 12 at the distal end of the insertion section 11, and the shape acquisition section 50a is not arranged in the long flexible tube portion 13 of the insertion section 11. Accordingly, the flexible tube portion 13 is not increased in diameter. It is thus possible to provide a flexible tube insertion apparatus comprising a small-diameter flexible tube portion 13 and achieving an improved ease of insertion.

By arranging the shape acquisition section 50a only in the bending portion 12, manufacturing costs can be reduced, compared to when the shape acquisition section 50a is arranged across the entire length of the insertion section 11. By changing the bending stiffness of the variable stiffness section 60 of each segment of the flexible tube portion 13 on the basis of the bending state of the bending portion 12, it is possible to improve the ease of insertion while reducing the cost.

The periodic change of the bending stiffness of the variable stiffness section 60 employed in the third embodiment may be combined with the present embodiment. It is thus possible to provide a flexible tube insertion apparatus that achieves an improved ease of insertion and conforms to complicated shapes of curvature in the intestinal tract.

Fifth Embodiment

The fifth embodiment of the present invention will be described with reference to FIGS. 15 and 16.

Figure 15:
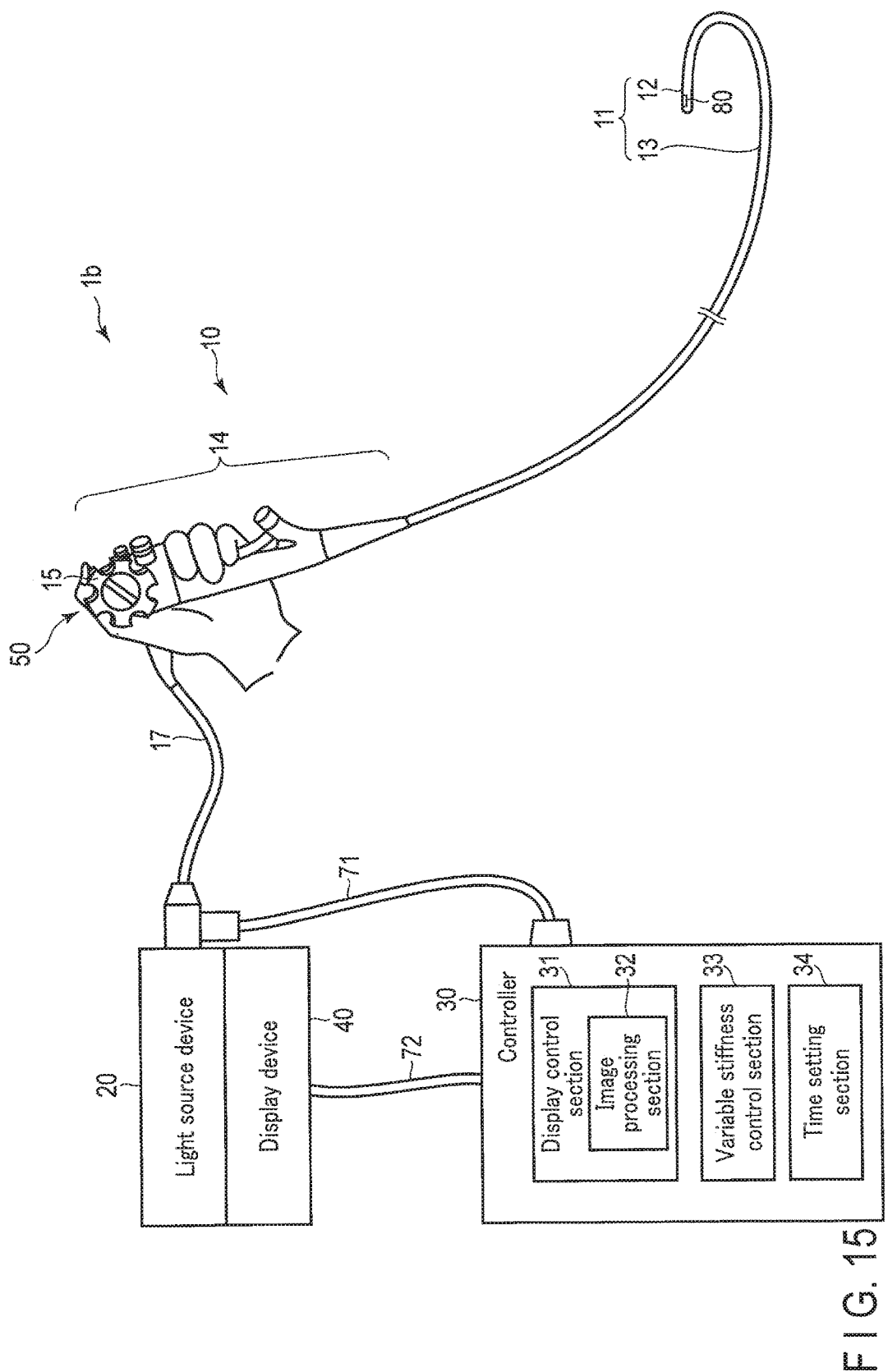
FIG. 15 is a diagram schematically showing a configuration of an endoscope apparatus according to a fifth embodiment.
Figure 16:
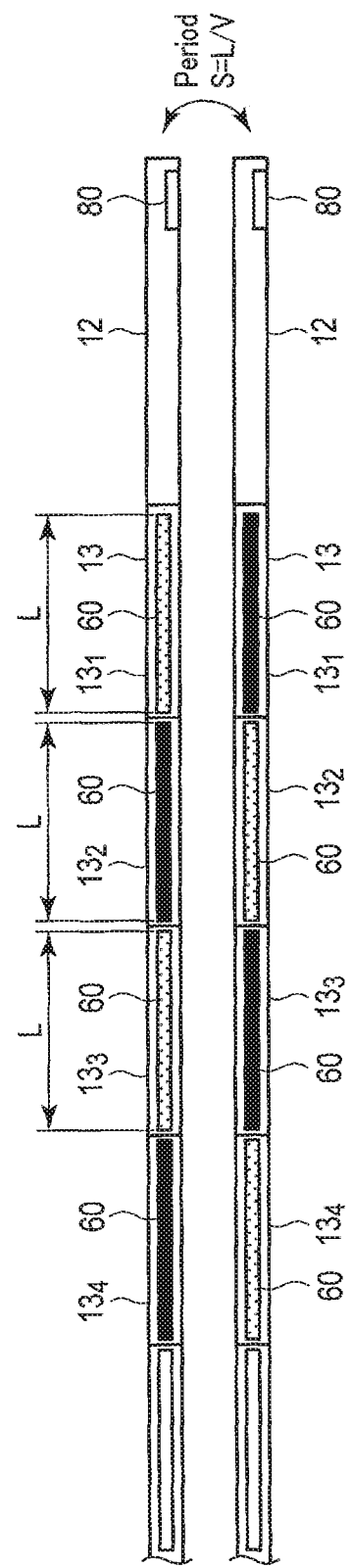
FIG. 16 is a diagram illustrating switching of a bending stiffness of variable stiffness sections according to the fifth embodiment.

FIG. 15 is a diagram schematically showing a configuration of an endoscope apparatus 1b according to the fifth embodiment. In the endoscope apparatus 1b, a distal speed detection section 80 is provided in the bending portion 12 located distally on the insertion section 11, in addition to the shape acquisition section 50 provided in the operation section 14. The distal speed detection section 80 is, for example, a known acceleration sensor that detects the rate of change of speed with respect to time. The distal speed detection section 80 is incorporated into the bending portion 12, for example, into the distal portion of the bending portion 12.

The controller 30 includes the time setting section 34, as in the third embodiment. However, the time setting section 34 in the present embodiment is different from that of the third embodiment in that the time setting section 34 is connected to the distal speed detection section 80 via the cable 71 and the distal speed detection signal cable included in the universal cord 17. Speed information of the bending portion 12 detected by the distal speed detection section 80 is output to the time setting section 34. The time setting section 34 sets a time T at which the bending stiffness of each of the variable stiffness sections 60 is periodically changed, that is, period S at which switching is made between stiff and soft states on the basis of the output speed information. In the present embodiment, the time T or period S is calculated by the time setting section 34 on the basis of the speed information of the bending portion 12 output from the distal speed detection section 80.

An example of the method of calculating the period S will be described. Let us assume that the longitudinal length of the variable stiffness section 60 in each segment of the flexible tube portion 13 is L, as shown in FIG. 16. Assuming that the speed of the bending portion 12 detected by the distal speed detection section 80 is V, the time setting section 34 calculates and sets the period S as S=L/V.

Of the steps of the variable stiffness control flow shown in FIG. 8, only the specific control of the variable stiffness control at step S15 is different in the fifth embodiment from that of the first embodiment, and the control is similar to that of the third embodiment. In the fifth embodiment, at step S15, the variable stiffness control section 33 reads out the time T or period S set by the time setting section 34. The variable stiffness control section 33 transmits a control signal for changing the bending stiffness of each variable stiffness section 60 to the variable stiffness sections 60 in such a manner that a variable stiffness section 60 with a low bending stiffness value and a variable stiffness section 60 with a high bending stiffness value are alternately arranged toward the proximal side of the flexible tube portion 13. Thereby, a soft segment 13₁ and 13₃ including a variable stiffness section 60 with a low bending stiffness value and a stiff segment 13₂ and 13₄ including a variable stiffness section 60 with a high bending stiffness value are alternately set in the flexible tube portion 13, as shown, for example, by the upper part in FIG. 16.

The variable stiffness control section 33 further transmits a control signal for changing the bending stiffness of each variable stiffness section 60 to the variable stiffness sections 60 to periodically switch the relationship of levels between the bending stiffness values of adjacent variable stiffness sections 60 at a time T or period S calculated by the time setting section 34 on the basis of speed information from the distal speed detection section 80. Thereby, a soft segment 13₁ and 13₃ including a variable stiffness section 60 with a high bending stiffness value, and a stiff segment 13₂ and 13₄ including a variable stiffness section 60 with a low bending stiffness value, are alternately set in the flexible tube portion 13 after the time T, as shown, for example, by the lower part in FIG. 16.

In the present embodiment, the distal speed detection section 80 is provided in the bending portion 12, and the time setting section 34 calculates the period S at which the bending stiffness is changed, on the basis of the speed of the bending portion 12 detected by the distal speed detection section 80. By thus changing the bending stiffness of each of the variable stiffness sections 60 on the basis of the speed of the bending portion 12, the bending stiffness can be changed in accordance with the movement of the bending portion 12. It is thus possible to provide a flexible tube insertion apparatus with an improved ease of insertion.

The present invention has been described above based on the embodiments and the variants thereof, but the present invention is not limited to those embodiments. The present invention may be modified and changed in various manners, without departing from the spirit and scope of the invention. For example, the flexible tube insertion apparatus is not limited to the endoscope apparatus 1, and includes a wide range of insertion apparatuses comprising a flexible insertion section.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube insertion apparatus comprising:
   an insertion section to be inserted into a subject and including a bending portion located distally on the insertion section, and a flexible tube portion located proximal to the bending portion;
   a plurality of variable stiffness sections each provided in a corresponding one of a plurality of segments defined in a longitudinal axis direction of the flexible tube portion and configured to cause a change in a level of a bending stiffness of the flexible tube portion on a segment-by-segment basis;
   a controller configured to:
      control the change in the bending stiffness of the flexible tube portion by the variable stiffness sections; and
      set a time period at which the bending stiffness is changed by the variable stiffness sections,
   wherein the controller controls the changes in the bending stiffness of each of the variable stiffness sections in such a manner that a relationship of levels between the bending stiffness of adjacent variable stiffness sections is switched at the set time period when the controller determines that the flexible tube portion is passing through a flexure of the subject based on a bending shape of the bending portion acquired from a shape acquisition sensor that acquires the bending shape of the bending portion and in such a manner that a variable stiffness section with a high bending stiffness value and a variable stiffness section with a low variable stiffness section are alternately arranged proximal to the flexible tube portion along the longitudinal axis direction.

2. The flexible tube insertion apparatus according to claim 1, wherein the controller performs a first bending state determination of determining whether or not the bending portion is bent to a predetermined degree or higher based on the bending shape of the bending portion acquired from the shape acquisition sensor, performs a second bending state determination of determining whether or not the bending portion is substantially straight after the first bending state determination determines that the bending portion is bent to the predetermined degree of higher, and determines that the flexible tube portion is passing through the flexure of the subject when the second bending state determination determines that the bending portion is substantially straight.

3. The flexible tube insertion apparatus according to claim 1, further comprising:
   the shape acquisition sensor,
      wherein the shape acquisition sensor is arranged in a bending operation section that is operated to bend the bending portion and acquires the bending shape of the bending portion based on an amount of operation of the bending operation section.

4. The flexible tube insertion apparatus according to claim 3, wherein the shape acquisition sensor is one or more of a magnetic sensor, an ultrasonic sensor, a fiber sensor, a distortion sensor, and a sensor using an X-ray absorbent material arranged in the bending portion.

5. The flexible tube insertion apparatus according to claim 1,
   wherein a distal speed detection sensor that detects a speed of the bending portion is provided in the bending portion, and
   the controller calculates the set time period based on the speed detected by the distal speed detection sensor.

6. A method of operating a flexible tube insertion apparatus including
   an insertion section to be inserted into a subject and including a bending portion located distally on the insertion section and a flexible tube portion located proximal to the bending portion, and a plurality of variable stiffness sections each provided in a corresponding one of a plurality of segments defined in a longitudinal axis direction of the flexible tube portion and configured to cause a change in a level of a bending stiffness of the flexible tube portion on a segment-by-segment basis, a controller configured to control the change in the bending stiffness of the flexible tube portion by the variable stiffness sections and set a time period at which the bending stiffness is changed by the variable stiffness sections,
the method comprising:
controlling the changes in the bending stiffness of each of the variable stiffness sections by the variable stiffness control section in such a manner that a relationship of levels between the bending stiffness of adjacent variable stiffness sections is switched at the set time period when the controller determines that the flexible tube portion is passing through a flexure of the subject based on a bending shape of the bending portion acquired from a shape acquisition sensor that acquires the bending shape of the bending portion and in such a manner that the variable stiffness section with a high bending stiffness value and the variable stiffness section with a low variable stiffness section are alternately arranged proximal to the flexible tube portion along the longitudinal axis direction.

* * * * *